United States Patent [19]

Sack

[11] Patent Number: 5,741,680

[45] Date of Patent: Apr. 21, 1998

[54] BUFFER COMPOSITION BASE AND METHOD OF FORMULATION FOR ORAL VACCINE DELIVERY

[75] Inventor: David A. Sack, Fallston, Md.

[73] Assignee: Cera Products, Inc., Columbia, Md.

[21] Appl. No.: 706,447

[22] Filed: Sep. 3, 1996

[51] Int. Cl.$^6$ .................. C12P 14/14; A61K 39/106; A01N 59/00; C12N 7/06
[52] U.S. Cl. .................. 435/99; 435/238; 424/261.1; 424/600; 424/717
[58] Field of Search .................. 435/99, 238; 424/261.1, 424/600, 717

[56] References Cited

U.S. PATENT DOCUMENTS

| | | |
|---|---|---|
| 4,152,413 | 5/1979 | Goodnow . |
| 4,251,509 | 2/1981 | Hanson et al. .................. 424/214.1 |
| 4,337,314 | 6/1982 | Oeschger et al. .................. 435/253 |
| 4,622,223 | 11/1986 | Schoolnik et al. .................. 424/92 |
| 4,661,350 | 4/1987 | Tsurumizu et al. .................. 424/92 |
| 4,681,762 | 7/1987 | Oeschger et al. .................. 424/92 |
| 4,752,474 | 6/1988 | Schneider .................. 424/224.1 |
| 4,876,096 | 10/1989 | Mitchell et al. . |
| 4,920,213 | 4/1990 | Dale et al. . |
| 4,927,628 | 5/1990 | Chanock et al. .................. 424/89 |
| 4,957,736 | 9/1990 | Nencioni et al. . |
| 5,000,952 | 3/1991 | Steinman et al. . |
| 5,001,225 | 3/1991 | Taylor . |
| 5,057,411 | 10/1991 | Lancaster et al. .................. 435/6 |
| 5,079,165 | 1/1992 | Clements et al. . |
| 5,147,646 | 9/1992 | Graham . |
| 5,176,909 | 1/1993 | Nerome et al. .................. 424/456 |
| 5,240,704 | 8/1993 | Tsurumizu et al. . |
| 5,242,820 | 9/1993 | Lo .................. 435/240 |
| 5,294,441 | 3/1994 | Curtiss, III . |
| 5,348,745 | 9/1994 | Daher .................. 424/466 |
| 5,352,448 | 10/1994 | Bowersock et al. .................. 424/438 |
| 5,364,756 | 11/1994 | Livesey et al. . |
| 5,419,907 | 5/1995 | Paul et al. .................. 424/221.1 |

*Primary Examiner*—Marian C. Knode
*Assistant Examiner*—Ali R. Salimi
*Attorney, Agent, or Firm*—Morton J. Rosenberg; David I. Klein; Jun Y. Lee

[57] ABSTRACT

This invention provides for a composition base and method of formulation to allow for oral vaccine delivery. The composition base is mixed with the oral vaccine and includes a carbohydrate composition having a dextrose equivalency value within the approximate range of 35–50. The buffer composition includes an electrolyte composition blended with the carbohydrate composition and the blended carbohydrate and electrolyte compositions are mixed each with respect to the other and then with the vaccine for oral ingestion by a user.

15 Claims, 2 Drawing Sheets

5,741,680

BUFFER COMPOSITION BASE AND METHOD OF FORMULATION FOR ORAL VACCINE DELIVERY

FIELD OF THE INVENTION

BACKGROUND OF THE INVENTION

This invention relates to buffer compositions used as a delivery system for products which are orally ingested. Further, this invention directs itself to a buffer composition for ingestible products which may be easily combined with the ingested food product prior to use, is easily formulated, and may be safely stored over long periods of time.

This invention is further directed specifically to a buffer composition and method of formulating the same which is designed for use as an oral vaccine delivery composition. The buffer composition base is mixed or otherwise blended with an oral vaccine prior to oral ingestion by a user or alternatively may be formulated to be added to the oral vaccine at the point of manufacture and stored in combined dosage form for later use. The specific formulations of the buffer composition are formed to act as a buffer which lowers the pH value of stomach acid which has been found to have a detrimental effect on the activity of the orally given vaccine. Additionally, the buffer composition provides a formulation which passes through the user's stomach in a rapid manner and allows the buffer fluid to be rapidly absorbed in the small intestine for establishing the vaccine antigens in close proximity to the intestinal mucosa.

PRIOR ART

Buffer compositions are known in the prior art. A number of buffer compositions are known in the prior art, some of which are shown in U.S. Pat. Nos. 5,242,820; 4,251,509; 5,352,448; 5,176,909; 4,752,474; 4,622,223; 5,057,411; 4,927,628; 4,661,350; 4,337,314; 4,681,762; 5,364,756; 4,957,736; 5,079,165; 5,000,952; 5,001,225; 5,240,704; 4,920,213; 5,147,646; 5,294,441; and, 4,152,413. However, none of these systems and compositions provide for a buffering composition which allows for an optimization of pH level reduction in the stomach while providing a rapid transfer of oral vaccine through the stomach itself.

A number of vaccines have constraints associated with them relating to the fact that their shelf life is rather low and that a number must be stored at refrigeration temperatures. Optimally a vaccine should have a long shelf life when stored at room temperatures. However, live vaccines tend to requires storage at cold temperatures even if the vaccine is lyophilized, due to the fact that the number of viable vaccine units drops with prolonged storage at warmer temperatures. Obviously, killed or dead vaccines are more stable than live vaccines however, such may also be destroyed by high temperatures. It is known that the chemical structure of proteins may be stabilized if they are stored in combination with certain sugars. Thus, commercially available enzymes are routinely stored with sugars to preserve their chemical structure however, the sugars which have been used are generally not applicable as buffering agents and have not been applied to vaccine antigens.

In general, only a few vaccines are administered orally, the only commonly used oral vaccine being oral polio vaccine consisting of attenuated polio viruses. Although the vaccine virus may be killed by acid conditions in the stomach, the vaccine has been formulated in a manner that sufficient viable virus particles pass through the stomach to be active in the small intestine. Presently, an oral typhoid vaccine is also available which consists of freeze-dried bacteria in an enteric-coated capsule formed in a manner such that the capsule does not dissolve until it reaches the alkaline pH of the small intestine.

The subject composition and method of formulation has been designed for immediate use with oral killed cholera vaccine. The cholera vaccine includes killed whole cells of cholera bacteria formed with the B subunit of the cholera toxin. The presently available cholera vaccine is currently formulated as a liquid with 3 or 4 ml of vaccine per dose which is stored in a cold room but not in its frozen form. The cholera vaccine is added to water containing buffer salts with the most common being Samarin, a commercially available effervescent antacid, although other salts have been used. The difficulties with the cholera vaccine as currently formulated includes handling of the liquid since the containers are bulky and in multi-dose bottles, the proper dosing has been difficult and resulted in wastage whereas single-dose vials have been found to be expensive and economically deficient. Additionally, in using such prior art buffers with the cholera vaccine, a constantly continuous cold chain is required in that the vaccine must be maintained in a cold state from the time of manufacture until it is orally ingested by the user. This has resulted in increased costs, shipping, storage and distribution which is a major advantage of the subject buffer composition since it may be formulated in dry particulate form to be added to the vaccine at the time of ingestion. Additionally, with the use of the current buffers available for the cholera vaccine, two separate ingredients such as the buffer and vaccine along with the materials for their use are needed rather than a single component, which complicates the distribution and accurate dispensing of the vaccine.

Finally, with regard to buffers used for the cholera vaccine as they now exist, such have been found to result in diarrhea among some of the persons taking the vaccine. Although not completely understood, it is believed that the diarrhea is due to a high osmolality of the buffer acting as an osmotic laxative. Although the diarrhea observed may be termed a side effect, it may also lessen immunogenicity if the vaccine antigens are swept out of the intestine before they have a chance to contact the antigen sampling cells. Lactose has also been found in some buffers which contributes to diarrhea in lactase deficient persons even though the amount of lactose in the prior art buffers is maintained at a low value.

The subject composition diminishes the disadvantages of the prior art in that it is simply a mixture of salts with a substrate such as rice syrup to which is added the vaccine antigens for the oral administration to the user. The salts are provided in predetermined concentrations to achieve neutralization of stomach acid for a sufficient time to allow the vaccine antigens to pass through the stomach.

The substrate maximizes absorption of the solution, thus preventing diarrhea and possible loss of vaccine effectiveness. Additionally, the substrate increases sodium and water uptake to aid in the prevention of diarrhea.

SUMMARY OF THE INVENTION

This invention directs itself to a buffer composition base and method of formulating such for oral vaccine delivery and includes a carbohydrate composition having a predetermined weight percentage of the buffer composition. The carbohydrate composition is formulated to have a dextrose equivalency value within the approximate range of 35–50. An electrolyte composition is blended with the carbohydrate composition and is added in a predetermined weight percentage of the overall buffer composition with the blended carbohydrate and electrolyte compositions being mixed with the vaccine for oral ingestion by a user.

DESCRIPTION OF THE PREFERRED EMBODIMENTS

Figure 1:
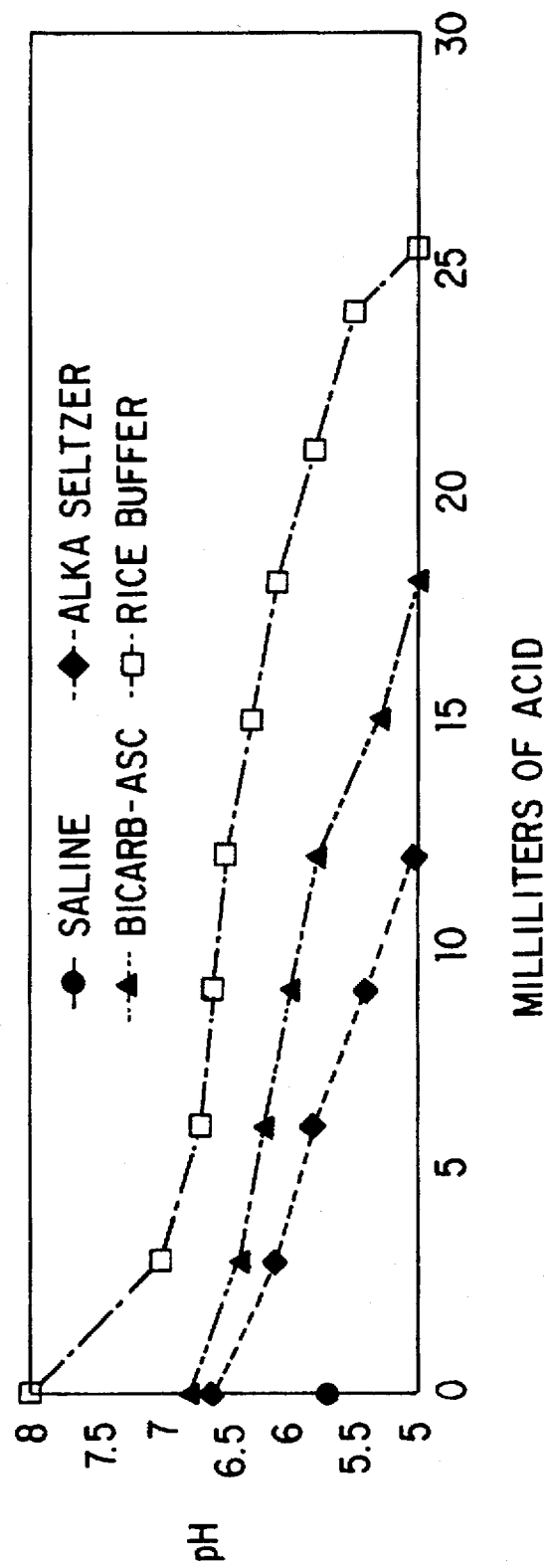
FIG. 1 is a graphical representation of the amount of stomach acid which may be neutralized to a pH value of 5.0 comparing a saline solution; a buffer composition base as herein described; Alka Seltzer (a registered Trademark); and a standard buffer including sodium bicarbonate and ascorbic acid; and, FIG. 2 is a bar graph showing vibriocidal serum antibody titers in patients immunized with a particular oral cholera vaccine as a function of time from immunization comparing a saline solution, a buffer composition base as herein described; Alka Seltzer (a registered Trademark); and a standard buffer including sodium bicarbonate and ascorbic acid.

Referring now to the inventive concept as herein described, there is provided a buffer composition base for oral vaccine delivery which includes a carbohydrate composition derived from food products such as starch containing food products in the form of rice, wheat, potatoes, corn or like food products where the carbohydrate composition formed therefrom for use in the buffer composition provides a dextrose equivalency value within the approximating range of 35–50. Additionally, the buffer composition base includes an electrolyte composition blended with the carbohydrate composition in a predetermine weight percentage value to be further described in following paragraphs.

The buffer composition and method of forming same as described in following paragraphs is specifically useful when mixed with an oral vaccine for oral ingestion by a user. A buffer composition base is particularly designed to act as a buffer to counteract stomach acid which would in general destroy some or all of the activity of vaccines which are administered orally. Thus, in concept, the subject buffer composition base is formed to preserve the vaccine during its passage through the stomach. Additionally, the buffer composition base as herein described may be initially blended with the vaccines for long-term storage in a dry form to act as a preservative for vaccine antigens during their storage at room temperature.

The subject buffer composition base may be formed as a powder which is added to water to prepare a buffer solution to which the oral vaccine is blended prior to oral ingestion by the user. Additionally, the buffer composition base may be used as a constituent of the particular vaccine where the buffer composition base is blended to the vaccine to provide a total powdered vaccine. In this mode of operation, the vaccine antigens may be packaged with the buffer composition base and administered in a single does manner. In this type of use, the buffer composition base serves the dual purpose of a stabilizer for the vaccine antigens during any long-term storage as well as a stomach acid neutralizing buffer when the vaccine and buffer composition combination is blended with water.

The subject buffer composition base is specifically formulated as a vaccine buffer and it is not believed that any other buffer composition has been formulated especially for this purpose. There are commercial antacids which may bind and neutralize vaccine antigens making them generally unsuitable as vaccine buffers. Sodium bicarbonate, commonly used as an antacid, when used by itself may raise the stomach pH to an excessive value, resulting in rebound stomach acid production. However, the buffer composition base as herein described only raises the gastric pH values to moderate levels resulting in the protection of the vaccine antigens for a generally extended period of time sufficient for the vaccine antigens to pass through the stomach. The subject buffer composition base is extremely important in its composition content of the carbohydrate composition and blended electrolyte composition for protection from stomach acid, which is a critical factor in the vaccine introduction to the user's body. The protection from stomach acid is critical with regard to both rapid gastric emptying as well as acid neutralization. The rapid gastric emptying is extremely important since if the vaccine progresses through the stomach quickly, there is less time for acid to destroy the vaccine antigens. Acid neutralization obviously is of extreme importance due to the fact that the antigens must be protected from the stomach acid until they proceed to the intestine. If a formulation buffer is used such that the vaccine pools in the intestine for a prolonged period of time or if the stomach acid is not neutralized, there is a significant loss in immunogenicity. The subject buffer composition provides for both rapid gastric emptying and appropriate stomach acid neutralization.

Testing of the buffer composition base as herein described has been found to facilitate antigen processing in the gut since it provides for passage of the vaccine through the stomach in a rapid manner in combination with the buffer neutralizing acid to preserve the vaccine antigens. It has also been found that the buffer composition appears to be rapidly absorbed in the small intestine due to the fact that the vaccine antigens come in close proximity to the intestinal mucosa.

Hypertonic solutions which have been used take an extended period of time to pass through the stomach and have also been found to draw fluid into the intestine, thus resulting in a diluted vaccine and limiting the vaccine's access to the mucosa.

The main constituent of the buffer composition base as herein described is a carbohydrate composition formed from a starch containing food product such as rice, wheat, corn, potatoes, or like food products which are processed to a dextrose equivalency value within the approximate range of 35–50. The food product is generally in dry form and is ground initially into particulate matter. The food product particulate matter is then added to water and is cooked for a predetermined time (dependent upon the food product used) and is then treated with enzymes to obtain a syrup with a dextrose equivalency value found to be within the approximating range of 35–50.

The enzyme may be a saccharifying enzyme, for example, a glucosidase enzyme such as glycoamylass, E.C.3.2.1.3 1,4-alpha-D-Glucan having a unit activity approximating 200 Diazyme Units per ml. which may be obtained under the Tradename Diazyme from Miles Laboratories, Inc., Elkhart, Ind. In the preferred embodiment of the buffer composition of the subject invention about 440 to about 2,200 Diazyme Units of the glucosidase enzyme are used in the saccharifying step per kilogram of whole grain rice.

The time of heating or cooking embed enzyme treatment of the food product determines whether the composition directs itself more to a glucose composition, maltose composition or malto-dextrin composition. The subject buffer composition base is formed to be a malto-dextrin composition having a carbohydrate chain which yields a dextrose equivalency value between 35–50. To the carbohydrate composition there is blended the electrolyte composition which in itself includes a first electrolyte composition chosen from the group consisting of trisodium citrate and citric acid as well as encompassing mixtures thereof, and a second neutralizing salt composition chosen from the group of sodium bicarbonate and calcium carbonate as well as mixtures thereof.

The carbohydrate composition in the buffer composition has been found useful within the approximate weight range of 50.0%–87.5% of the total weight of the buffer composition. The electrolyte composition comprising both the first electrolyte composition and second neutralizing salt composition has been found useful within the approximate range of 12.5%–50.0% of the overall weight of the buffer composition. A further breakdown of the useful buffer composition weight percentages has been determined that the first electrolyte composition formed of trisodium citrate and/or citric acid as well as mixtures thereof has been found useful in the percentage range of 2.5%–10.0% of the overall buffer composition weight, with the neutralizing salt composition formed from sodium bicarbonate and/or calcium carbonate being useful within the range of 10.0%–40.0% of the overall buffer composition.

After testing, a particular percentage ratio has been found to be optimum and includes a carbohydrate composition weight approximating 73.7% with the overall electrolyte composition weight approximating 26.3% of the total buffer composition weight. Further breakdown show the preferred weight percentage of the overall electrolyte composition to be preferably a first electrolyte composition approximate weight of 5.2% and a neutralizing salt composition weight approximating 21.1% of the overall buffer composition.

Once the proper composition has been formed, the method of forming the overall buffer composition for oral vaccine delivery includes the step of generally heating the starch containing food product in an aqueous solution to form a carbohydrate composition having a dextrose equivalency as stated previously within the approximating range of 35–50. Subsequent to this, the electrolyte composition consisting of the first electrolyte composition and the neutralizing salt is blended into the carbohydrate composition.

The starch containing food product generally is derived from food products such as corn, rice, wheat, potatoes, or like food products which may be brought to a dextrose equivalency between 35–50.

The step of heating the starch containing food product is generally preceded by a grinding step which grinds the food product, whether it be rice, wheat, potatoes or corn, into a particulate type of composition. The particulates are treated with enzymes as previously described and then added to water for heating. Subsequent to the initiation of the heating step, the electrolyte composition is added until the overall buffer composition attains a somewhat viscous state.

When used in dry form, the buffer composition is dried through spray drying, drum dried or freeze-dried, not important to the inventive concept as herein described, with the exception that the resulting buffer composition is substantially dry and in powdered form.

In order to test the advantages of the subject buffer composition, it was determined that the use of the subject buffer composition neutralized a much larger amount of acid than the standard or previously used buffers. Referring to FIG. 1, such relates the testing of four separate buffers with the object being to reduce the pH level of hydrochloric acid to a level of 5.0. As shown in the Figure, four separate buffers were used, namely: (1) normal saline; (2) rice buffer which is a preferred embodiment of the subject buffer composition which was formed in the composition weights of 2.0 grams of sodium bicarbonate to 0.5 grams of trisodium citrate and 7.0 grams of rice syrup solids; (3) Alka Seltzer (a registered Trademark), which is a commercially known buffering agent; and, (4) what is termed a "standard buffer" which consisted of 2.5 grams of sodium bicarbonate to 1.8 grams of ascorbic acid. The volume in the test was 150 ml with each buffer. In the test, each of the buffers were prepared in the amount of 150 ml and measured volumes of acid were added in the form of hydrogen chloride. The acid was added until the pH level was reduced to 5.0.

Responsive to the testing, it is seen from the Figure that a dose of the subject buffer composition neutralized 25.4 ml of acid whereas the "standard buffer" consisting of sodium bicarbonate and ascorbic acid, neutralized 15.5 ml of acid. The two remaining buffers, namely, the Alka Seltzer (registered Trademark) composition, reduced 8 ml of acid, and the saline solution approximately 3 ml of acid.

BUFFER STUDY

A study has been made in order to compare the immunogenicity of a relatively new oral live cholera vaccine (Peru 15) when the vaccine is given with different buffers. Peru 15 is a candidate live oral cholera vaccine developed at the Virus Research Institute and is being currently tested at Johns Hopkins University Vaccine Testing Unit. Peru 15 is an El Tor strain of vibrio cholerae which is non-virulent since it does not produce toxin and is non-motile. The vaccine produces the B subunit of the toxin and may induce antitoxic as well as antibacterial immunity.

The protocol of the study was designed to provide data as to a comparison between: (1) a sodium bicarbonate and ascorbic acid buffer; (2) a commercially available buffer (STANDARD BUFFER) Alka-Seltzer (registered Trademark); (3) a buffer of the subject invention concept using a combination of rice syrup solids, sodium bicarbonate and trisodium citrate (RICE BUFFER). These three buffers were compared to saline which has no or little buffering capacity.

Thirty-nine (39) volunteers were recruited to participate in a blind, randomized, four cell, outpatient study to determine the immunogenicity of Peru 15 oral cholera vaccine when given with one of the three aforementioned buffers as well as saline.

All volunteers were given a single dose ($10^8$ lyophilized bacterial cells of Peru 15 live oral cholera vaccine) with one of the four aforementioned compositions.

The four buffering compositions used in the study are provided in Table 1 showing the ingredients with the grams per dose of each ingredient and the dosage level. The volume of dosage level was 100 ml for the sodium bicarbonate and ascorbic acid (STANDARD BUFFER) combination since this was the volume used in previous protocols with 150 ml being used with the other buffers since the rice buffer which is the carbohydrate composition with the salts having been designed to have a higher volume to avoid hypertonicity. The carbohydrate composition with salts was formulated having a dextrose equivalency value of 42.

TABLE 1

| BUFFER | INGREDIENTS (GRAMS/DOSE) | | DOSE |
|---|---|---|---|
| 1. STANDARD BUFFER | SODIUM BICARBONATE ASCORBIC ACID | (2.5) (1.8) | 100 ml |
| 2. ALKA SELTZER (registered Trademark) | SODIUM BICARBONATE CITRIC ACID POTASSIUM BICARBONATE | (1.9) (1.66) (0.62) | 150 ml |
| 3. CARBOHYDRATE COMPOSITION WITH SALTS | SODIUM BICARBONATE TRISODIUM CITRATE RICE SYRUP SOLIDS | (2.0) (0.5) (7.0) | 150 ml |
| 4. SALINE | SODIUM CHLORIDE | (1.35) | 150 ml |

Fecal specimens were collected after seven, ten, fourteen and twenty-one days after an initial dosage. Two swabs were collected, with one being placed in a vial of alkaline peptone water and the other in a vial of sterile phosphate buffered saline. The vials were inoculated onto TCBS agar overnight however, in the case of the alkaline peptone water, the vial was incubated for six hours before inoculation onto the TCBS. Colonies which were suspected to be vibrios were confirmed using oxidase reagent and Serotype O1 specific antiserum. From each positive specimen ten colonies were tested in motility agar to detect any colonies which might have reverted to being motile.

Ten ml of blood was collected for serology prior to vaccination on the tenth and twenty-first day. Vibriocidal and antitoxin assays were carried out in the laboratory of the vaccine testing unit at Johns Hopkins University according to standard procedures.

The results of the study were classified as follows: (1) a significant antibody response was defined as a four-fold increase for vibriocidal and two-fold increase for antitoxin; (2) a high vibriocidal response was one defined where there was a significant increase to a titer exceeding 1:1000; and, (3) a high toxin response was defined as a titer which increased more than four-fold.

The results of the vibriocidal assays are shown in Table 2 with the group receiving saline having fewer vibriocidal responses than the other groups. The fold-increase in vibriocidal responses was highest in those patients receiving the rice buffer followed by those receiving the Alka Seltzer. Nine of ten patients receiving the rice buffer had a higher response, while lower proportions were seen with the other buffers.

TABLE 2

VIBRIOCIDAL RESPONSES

| TYPE RESPONSE | SODIUM BICARBONATE & ASCORBIC ACID | ALKA SELTZER | RICE BUFFER | SALINE |
|---|---|---|---|---|
| SIGNIFICANT RESPONSE | 10 | 10 | 10 | 4 |
| HIGH RESPONSE | 4 | 6 | 9 | 3 |
| NO. IN TEST | 10 | 10 | 10 | 9 |

Figure 2:
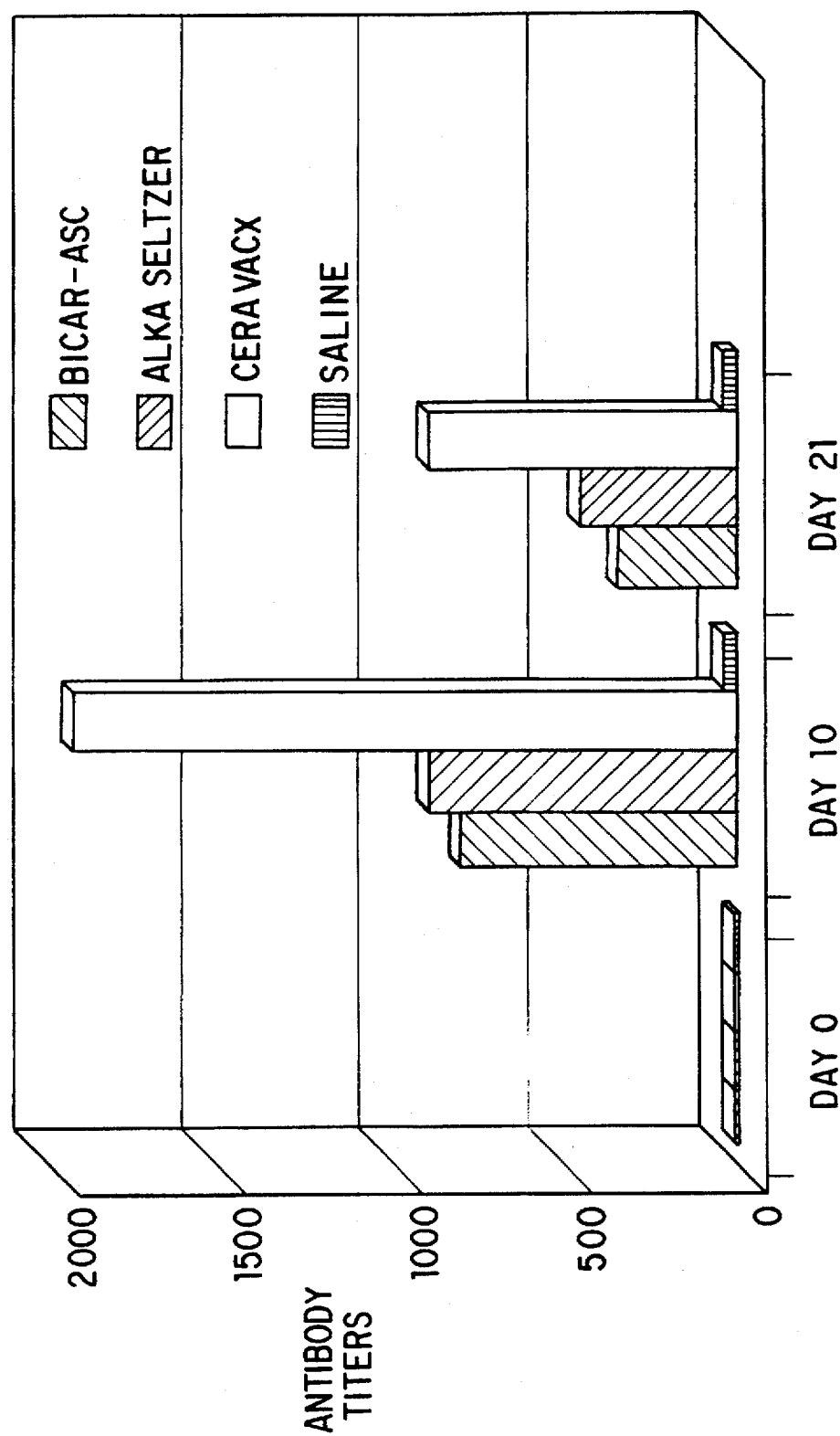

FIG. 2 is a bar graph showing vibriocidal serum antibody titers in the volunteers immunized with Peru 15 (oral cholera vaccine) as a function of time subsequent to immunization comparing the above-referenced buffers. The values shown in FIG. 2 are shown as the geometric means and are provided for day 0, 10 and 21 subsequent to immunization.

Antitoxin responses according to the buffer received are shown in Table 3. Two-fold increases in antitoxin were observed in thirteen of the thirty patients receiving vaccine with buffer and one of nine who received the saline.

TABLE 3

ANTITOXIN RESPONSES

| TYPE RESPONSE | SODIUM BICARBONATE & ASCORBIC ACID | ALKA SELTZER | RICE BUFFER | SALINE |
|---|---|---|---|---|
| SIGNIFICANT RESPONSE (>2 FOLD) | 4 | 5 | 4 | 1 |
| HIGH RESPONSE (>4 FOLD) | 2 | 3 | 2 | 1 |
| NO. IN TEST | 10 | 10 | 10 | 9 |

Among the groups who received the vaccine with the sodium bicarbonate and ascorbic acid; or Alka-Seltzer; or rice buffer composition, the highest vibriocidal response was seen with the rice buffer. In this group, nine of ten had a high titer and the geometric mean titer post-vaccine was 1:1940, which was more than twice as high as the other two buffers used. The mean fold increase in the rice-buffer group was 194-fold increase compared to a 64-fold and 111-fold increase in the bicarbonate and ascorbic acid group and the Alka Seltzer group respectively.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A buffer composition base suitable for mixing with an oral vaccine comprising:
   (a) a carbohydrate composition having a weight percentage of said buffer composition within the approximate weight range of 40.0%–87.5%, said carbohydrate composition formed from a starch containing food product and having a dextrose equivalency value approximating 41; and,
   (b) an electrolyte composition blended with said carbohydrate composition and forming a weight percentage of said buffer composition within the approximate range of 12.5%–50.0%, said blended carbohydrate and electrolyte compositions being mixed with said vaccine for oral ingestion by a user, said electrolyte composition including a first electrolyte composition chosen from the group consisting of trisodium citrate, citric acid and mixtures thereof, and said electrolyte composition further including a second neutralizing salt composition chosen from the group consisting of sodium bicarbonate, calcium carbonate and mixtures thereof.

2. The buffer composition as recited in claim 1 where said carbohydrate composition is formed from a food composition chosen from the group consisting of rice, wheat, corn, potatoes and mixtures thereof.

3. The buffer composition as recited in claim 1 where said first electrolyte composition predetermined weight percentage is within the approximate range of 2.5%–10.0% of said buffer composition.

4. The buffer composition as recited in claim 1 where said second neutralizing salt composition predetermined weight percentage is within the approximate range of 10.0%–40% of said buffer composition.

5. The buffer composition as recited in claim 1 where said carbohydrate composition weight percentage is approximately 73.7% of said buffer composition, and said electrolyte composition weight percentage is 26.3% of said buffer composition.

6. The buffer composition as recited in claim 4 where said first electrolyte composition weight percentage is approximately 5.2% of said buffer composition and said second neutralizing salt composition weight percentage is approximately 21.1% of said buffer composition.

7. A method of forming a buffer composition for oral vaccine delivery including the steps of:
   (a) heating a starch containing food product treated with a glucosidase enzyme composition in an aqueous solution to form a carbohydrate composition; and,
   (b) blending an electrolyte composition into said carbohydrate composition.

8. The method of forming a buffer composition as recited in claim 7 where the step of heating said starch containing food product is preceded by the step of grinding said starch containing food product to form particulates of said food product.

9. The method of forming a buffer composition as recited in claim 7 where the step of grinding is followed by the step of adding said particulates to water.

10. The method of forming a buffer composition as recited in claim 7 where said heated starch containing food product and said blended electrolyte composition form a viscous liquid buffer composition.

11. The method of forming a buffer composition as recited in claim 7 where said starch containing food product is chosen from the group consisting of rice, wheat, corn, and potatoes and mixtures thereof.

12. The method of forming a buffer composition as recited in claim 7 where said carbohydrate composition is within the approximate weight percentage range of 50%–87.5% of said buffer composition.

13. The method of forming a buffer composition as recited in claim 10 where said electrolyte composition is within the approximate weight percentage range of 12.5%–50.0% of said buffer composition.

14. The method of forming a buffer composition as recited in claim 7 where the step of blending an electrolyte composition includes the steps of:
   (a) providing a first electrolyte composition chosen from the group consisting of trisodium citrate and citric acid and mixtures thereof; and,
   (b) mixing a second neutralizing salt composition into said first electrolyte composition.

15. The method of forming a buffer composition as recited in claim 14 where said neutralizing salt composition is chosen from the group of sodium bicarbonate and calcium bicarbonate and mixtures thereof.

* * * * *